(12) United States Patent
Lindekugel (10) Patent No.: US 12,167,869 B2
(45) Date of Patent: Dec. 17, 2024

(54) FLEXIBLE INTRAOSSEOUS OBTURATOR

(71) Applicant: Bard Access Systems, Inc., Salt Lake City, UT (US)

(72) Inventor: Eric W. Lindekugel, Salt Lake City, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 221 days.

(21) Appl. No.: 17/183,820

(22) Filed: Feb. 24, 2021

(65) Prior Publication Data

US 2021/0267637 A1 Sep. 2, 2021

Related U.S. Application Data (60) Provisional application No. 62/983,434, filed on Feb. 28, 2020.

(51) Int. Cl.
*A61B 17/34* (2006.01)
(52) U.S. Cl.
CPC ...... *A61B 17/3472* (2013.01); *A61B 17/3423* (2013.01); *A61B 17/3496* (2013.01)
(58) Field of Classification Search
CPC ........................ A61B 17/3468; A61B 17/3472
See application file for complete search history.

(56) References Cited

U.S. PATENT DOCUMENTS

| | | | |
|---|---|---|---|
| 2,773,501 A | 12/1956 | Young | |
| 3,071,135 A | 1/1963 | Baldwin et al. | |
| 3,166,189 A | 1/1965 | Disston | |
| 3,329,261 A | 7/1967 | Serany, Jr. et al. | |
| D222,312 S | 10/1971 | Kurtz et al. | |
| 3,802,555 A | 4/1974 | Grasty et al. | |

(Continued)

FOREIGN PATENT DOCUMENTS

| | | | |
|---|---|---|---|
| EP | 0232600 A1 | 8/1987 | |
| EP | 0548612 A1 | 6/1993 | |

(Continued)

OTHER PUBLICATIONS

EP 17861304.8 filed Apr. 16, 2019 Extended European Search Report filed Jul. 28, 2020.

(Continued)

*Primary Examiner* — Nicholas W Woodall
(74) *Attorney, Agent, or Firm* — Rutan & Tucker LLP (57) ABSTRACT

Apparatus and methods for a flexible obturator for use with an access assembly of an intraosseous device are disclosed. The flexible obturator can include elastic properties and relatively low columnar strength, relatively low shear strength, and/or relatively high compressive strength. When the obturator is supported in the needle, the obturator can prevent bone fragments and tissue from blocking the needle lumen. When removed from the needle, the obturator can deform under a force to prevent accidental needle stick injuries. The flexible obturator can define a radially symmetrical profile and can conform to the inner profile of the needle lumen. The flexible obturator can extend beyond a distal tip of the needle and be trimmed flush to a beveled surface of the needle. This simplifies the manufacturing process, allowing a single size obturator to be fitted to multiple sizes of needle.

10 Claims, 6 Drawing Sheets

(56) References Cited

U.S. PATENT DOCUMENTS

| | | | |
|---|---|---|---|
| 3,815,605 A | 6/1974 | Schmidt et al. | |
| 3,991,765 A | 11/1976 | Cohen | |
| 4,010,737 A * | 3/1977 | Vilaghy | A61B 10/025 |
| | | | 30/316 |
| 4,153,160 A | 5/1979 | Leigh | |
| 4,226,328 A | 10/1980 | Beddow | |
| 4,266,555 A | 5/1981 | Jamshidi | |
| 4,314,565 A | 2/1982 | Lee | |
| 4,383,530 A | 5/1983 | Bruno | |
| 4,501,363 A | 2/1985 | Isbey, Jr. | |
| 4,595,102 A | 6/1986 | Cianci et al. | |
| 4,838,282 A | 6/1989 | Strasser et al. | |
| 4,889,529 A | 12/1989 | Haindl | |
| 4,925,448 A | 5/1990 | Bazaral | |
| 4,952,207 A | 8/1990 | Lemieux | |
| 4,964,854 A | 10/1990 | Luther | |
| 4,969,870 A | 11/1990 | Kramer et al. | |
| 5,040,542 A | 8/1991 | Gray | |
| 5,042,558 A | 8/1991 | Hussey et al. | |
| 5,053,017 A | 10/1991 | Chamuel | |
| 5,098,391 A | 3/1992 | Pantages et al. | |
| 5,122,114 A | 6/1992 | Miller et al. | |
| 5,207,697 A | 5/1993 | Carusillo et al. | |
| 5,263,939 A | 11/1993 | Wortrich | |
| 5,290,267 A | 3/1994 | Zimmermann | |
| 5,312,364 A | 5/1994 | Jacobs | |
| 5,322,163 A | 6/1994 | Foos | |
| 5,332,398 A | 7/1994 | Miller et al. | |
| 5,364,367 A | 11/1994 | Banks et al. | |
| 5,372,583 A | 12/1994 | Roberts et al. | |
| 5,406,940 A | 4/1995 | Melzer et al. | |
| 5,451,210 A | 9/1995 | Kramer et al. | |
| 5,525,314 A | 6/1996 | Hurson | |
| 5,554,154 A | 9/1996 | Rosenberg | |
| 5,575,780 A | 11/1996 | Saito | |
| 5,591,188 A | 1/1997 | Waisman | |
| 5,601,559 A | 2/1997 | Melker et al. | |
| 5,688,249 A | 11/1997 | Chang et al. | |
| 5,746,720 A | 5/1998 | Stouder, Jr. | |
| 5,772,678 A | 6/1998 | Thomason et al. | |
| 5,779,708 A | 7/1998 | Wu | |
| 5,807,275 A | 9/1998 | Jamshidi | |
| 5,810,738 A | 9/1998 | Thomas, II | |
| 5,810,826 A | 9/1998 | Ang et al. | |
| 5,817,052 A | 10/1998 | Johnson et al. | |
| 5,853,393 A | 12/1998 | Bogert | |
| 5,868,684 A | 2/1999 | .ANG.kerfeldt et al. | |
| 5,868,711 A | 2/1999 | Kramer et al. | |
| 5,871,470 A * | 2/1999 | McWha | A61B 17/3401 |
| | | | 604/158 |
| 5,885,293 A | 3/1999 | McDevitt | |
| 5,927,976 A | 7/1999 | Wu | |
| 5,947,890 A | 9/1999 | Spencer et al. | |
| 5,960,797 A | 10/1999 | Kramer et al. | |
| 5,967,143 A | 10/1999 | Klappenberger | |
| 5,990,382 A | 11/1999 | Fox | |
| 6,012,586 A | 1/2000 | Misra | |
| 6,068,121 A | 5/2000 | McGlinch | |
| 6,117,108 A | 9/2000 | Woehr et al. | |
| 6,135,769 A | 10/2000 | Kwan | |
| 6,210,373 B1 | 4/2001 | Allmon | |
| 6,210,376 B1 | 4/2001 | Grayson | |
| 6,228,088 B1 | 5/2001 | Miller et al. | |
| 6,247,928 B1 | 6/2001 | Meller et al. | |
| 6,273,715 B1 | 8/2001 | Meller et al. | |
| 6,419,490 B1 | 7/2002 | Kitchings Weathers, Jr. | |
| 6,458,117 B1 | 10/2002 | Pollins, Sr. | |
| 6,527,778 B2 | 3/2003 | Athanasiou et al. | |
| 6,602,214 B2 | 8/2003 | Heinz et al. | |
| 6,626,887 B1 | 9/2003 | Wu | |
| 6,629,959 B2 | 10/2003 | Kuracina et al. | |
| 6,641,395 B2 | 11/2003 | Kumar et al. | |
| 6,652,490 B2 | 11/2003 | Howell | |
| 6,692,471 B2 | 2/2004 | Boudreaux | |
| 6,761,726 B1 | 7/2004 | Findlay et al. | |
| 6,814,734 B2 | 11/2004 | Chappuis et al. | |
| 6,830,562 B2 | 12/2004 | Mogensen et al. | |
| 6,875,219 B2 | 4/2005 | Arramon et al. | |
| 6,905,486 B2 | 6/2005 | Gibbs | |
| 6,916,292 B2 | 7/2005 | Morawski et al. | |
| 6,984,213 B2 | 1/2006 | Horner et al. | |
| 6,991,096 B2 | 1/2006 | Gottlieb et al. | |
| 6,997,907 B2 | 2/2006 | Safabash et al. | |
| 7,112,191 B2 | 9/2006 | Daga | |
| 7,135,031 B2 | 11/2006 | Flint | |
| 7,179,244 B2 | 2/2007 | Smith et al. | |
| 7,214,208 B2 | 5/2007 | Vaillancourt et al. | |
| 7,278,987 B2 | 10/2007 | Solazzo | |
| 7,347,838 B2 | 3/2008 | Kull | |
| 7,347,840 B2 | 3/2008 | Findlay et al. | |
| 7,399,306 B2 | 7/2008 | Reiley et al. | |
| 7,407,493 B2 | 8/2008 | Cane' | |
| 7,410,053 B2 | 8/2008 | Bowen et al. | |
| 7,434,687 B2 | 10/2008 | Itou et al. | |
| 7,458,954 B2 | 12/2008 | Ferguson et al. | |
| 7,513,888 B2 | 4/2009 | Sircom et al. | |
| 7,530,965 B2 | 5/2009 | Villa et al. | |
| 7,534,227 B2 | 5/2009 | Kulli | |
| 7,569,033 B2 | 8/2009 | Greene et al. | |
| 7,582,102 B2 | 9/2009 | Heinz et al. | |
| 7,588,559 B2 | 9/2009 | Aravena et al. | |
| 7,658,725 B2 | 2/2010 | Bialecki et al. | |
| 7,670,328 B2 | 3/2010 | Miller | |
| 7,699,807 B2 | 4/2010 | Faust et al. | |
| 7,699,850 B2 | 4/2010 | Miller | |
| 7,736,332 B2 | 6/2010 | Carlyon et al. | |
| 7,743,918 B2 | 6/2010 | Itou et al. | |
| 7,749,225 B2 | 7/2010 | Chappuis et al. | |
| 7,798,994 B2 | 9/2010 | Brimhall | |
| 7,811,260 B2 | 10/2010 | Miller et al. | |
| 7,815,642 B2 | 10/2010 | Miller | |
| 7,828,773 B2 | 11/2010 | Swisher et al. | |
| 7,828,774 B2 | 11/2010 | Harding et al. | |
| 7,833,204 B2 | 11/2010 | Picha | |
| 7,842,038 B2 | 11/2010 | Haddock et al. | |
| 7,850,620 B2 | 12/2010 | Miller et al. | |
| 7,850,650 B2 | 12/2010 | Breitweiser | |
| D633,199 S | 2/2011 | MacKay et al. | |
| 7,899,528 B2 | 3/2011 | Miller et al. | |
| 7,900,549 B2 | 3/2011 | Kobayashi | |
| 7,905,857 B2 | 3/2011 | Swisher | |
| 7,951,089 B2 | 5/2011 | Miller | |
| 7,955,297 B2 | 6/2011 | Radmer et al. | |
| 7,972,339 B2 | 7/2011 | Nassiri et al. | |
| 7,976,498 B2 | 7/2011 | Swisher et al. | |
| 7,976,502 B2 | 7/2011 | Baid | |
| 8,038,664 B2 | 10/2011 | Miller et al. | |
| 8,043,253 B2 | 10/2011 | Kraft et al. | |
| 8,043,265 B2 | 10/2011 | Abe et al. | |
| 8,096,973 B2 | 1/2012 | Snow et al. | |
| 8,142,365 B2 | 3/2012 | Miller | |
| 8,152,771 B2 | 4/2012 | Mogensen et al. | |
| 8,162,904 B2 | 4/2012 | Takano et al. | |
| 8,167,899 B2 | 5/2012 | Justis et al. | |
| 8,231,547 B2 | 7/2012 | Deck et al. | |
| 8,235,945 B2 | 8/2012 | Baid | |
| 8,240,468 B2 | 8/2012 | Wilkinson et al. | |
| 8,246,584 B2 | 8/2012 | Aravena et al. | |
| 8,273,053 B2 | 9/2012 | Saltzstein | |
| 8,292,891 B2 | 10/2012 | Browne et al. | |
| 8,308,693 B2 | 11/2012 | Miller et al. | |
| 8,333,769 B2 | 12/2012 | Browne et al. | |
| 8,356,598 B2 | 1/2013 | Rumsey | |
| 8,357,163 B2 | 1/2013 | Sidebotham et al. | |
| 8,388,623 B2 | 3/2013 | Browne et al. | |
| 8,414,539 B1 | 4/2013 | Kuracina et al. | |
| 8,419,683 B2 | 4/2013 | Miller et al. | |
| 8,480,632 B2 | 7/2013 | Miller et al. | |
| 8,480,672 B2 | 7/2013 | Browne et al. | |
| 8,486,027 B2 | 7/2013 | Findlay et al. | |
| 8,506,568 B2 | 8/2013 | Miller | |
| 8,529,576 B2 | 9/2013 | Krueger et al. | |
| 8,535,271 B2 | 9/2013 | Fuchs et al. | |
| 8,562,615 B2 | 10/2013 | Browne et al. | |

(56) References Cited

U.S. PATENT DOCUMENTS

| | | |
|---|---|---|
| 8,584,849 B2 | 11/2013 | McCaffrey |
| 8,641,715 B2 | 2/2014 | Miller |
| 8,647,257 B2 | 2/2014 | Jansen et al. |
| 8,656,929 B2 | 2/2014 | Miller et al. |
| 8,657,790 B2 | 2/2014 | Tal et al. |
| 8,662,306 B2 | 3/2014 | Agrawal |
| 8,663,231 B2 | 3/2014 | Browne et al. |
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 8,758,383 B2 | 6/2014 | Geist |
| 8,771,230 B2 | 7/2014 | White et al. |
| 8,801,663 B2 | 8/2014 | Woehr |
| 8,812,101 B2 | 8/2014 | Miller et al. |
| 8,814,835 B2 | 8/2014 | Baid |
| 8,828,001 B2 | 9/2014 | Stearns et al. |
| 8,870,872 B2 | 10/2014 | Miller |
| 8,893,883 B2 | 11/2014 | Valaie et al. |
| D720,471 S | 12/2014 | Angel et al. |
| 8,936,575 B2 | 1/2015 | Moulton |
| 8,944,069 B2 | 2/2015 | Miller et al. |
| 8,974,410 B2 | 3/2015 | Miller et al. |
| 8,998,848 B2 | 4/2015 | Miller et al. |
| 9,072,543 B2 | 7/2015 | Miller et al. |
| 9,078,637 B2 | 7/2015 | Miller |
| 9,131,925 B2 | 9/2015 | Kraft et al. |
| 9,149,625 B2 | 10/2015 | Woehr et al. |
| 9,173,679 B2 | 11/2015 | Tzachar et al. |
| 9,186,217 B2 | 11/2015 | Goyal |
| 9,226,756 B2 | 1/2016 | Teisen et al. |
| 9,278,195 B2 | 3/2016 | Erskine |
| 9,295,487 B2 | 3/2016 | Miller et al. |
| 9,302,077 B2 | 4/2016 | Domonkos et al. |
| 9,314,232 B2 | 4/2016 | Stark |
| 9,314,270 B2 | 4/2016 | Miller |
| 9,358,348 B2 | 6/2016 | Weilbacher et al. |
| 9,393,031 B2 | 7/2016 | Miller |
| 9,414,815 B2 | 8/2016 | Miller et al. |
| 9,415,192 B2 | 8/2016 | Kuracina et al. |
| 9,421,345 B2 | 8/2016 | Woehr et al. |
| 9,427,555 B2 | 8/2016 | Baid |
| 9,433,400 B2 | 9/2016 | Miller |
| 9,439,667 B2 | 9/2016 | Miller |
| 9,439,702 B2 | 9/2016 | Arthur et al. |
| 9,451,968 B2 | 9/2016 | Miller et al. |
| 9,451,983 B2 | 9/2016 | Windolf |
| 9,480,483 B2 | 11/2016 | Browne et al. |
| 9,486,604 B2 | 11/2016 | Murray et al. |
| 9,504,477 B2 | 11/2016 | Miller et al. |
| 9,545,243 B2 | 1/2017 | Miller et al. |
| 9,615,816 B2 | 4/2017 | Woodard |
| 9,615,838 B2 | 4/2017 | Nino et al. |
| 9,623,210 B2 | 4/2017 | Woehr |
| 9,636,484 B2 | 5/2017 | Baid |
| 9,681,889 B1 | 6/2017 | Greenhalgh et al. |
| 9,687,633 B2 | 6/2017 | Teoh |
| 9,717,564 B2 | 8/2017 | Miller et al. |
| 9,730,729 B2 | 8/2017 | Kilcoin et al. |
| 9,744,333 B2 | 8/2017 | Terzibashian |
| 9,782,546 B2 | 10/2017 | Woehr |
| 9,788,843 B2 | 10/2017 | Teisen et al. |
| 9,839,740 B2 | 12/2017 | Beamer et al. |
| 9,844,646 B2 | 12/2017 | Knutsson |
| 9,844,647 B2 | 12/2017 | Knutsson |
| 9,872,703 B2 | 1/2018 | Miller et al. |
| 9,883,853 B2 | 2/2018 | Woodard et al. |
| 9,895,512 B2 | 2/2018 | Kraft et al. |
| 9,962,211 B2 | 5/2018 | Csernatoni |
| 9,999,444 B2 | 6/2018 | Geist et al. |
| 10,022,464 B2 | 7/2018 | Sarphati et al. |
| 10,039,897 B2 | 8/2018 | Norris et al. |
| 10,052,111 B2 | 8/2018 | Miller et al. |
| 10,064,694 B2 | 9/2018 | Connolly |
| 10,070,933 B2 | 9/2018 | Adler et al. |
| 10,070,934 B2 | 9/2018 | Kerns et al. |
| 10,080,864 B2 | 9/2018 | Terzibashian |
| 10,092,320 B2 | 10/2018 | Morgan et al. |
| 10,106,295 B2 | 10/2018 | Lockwood |
| 10,130,343 B2 | 11/2018 | Miller et al. |
| 10,136,878 B2 | 11/2018 | Tzachar et al. |
| 10,182,878 B2 | 1/2019 | Goyal |
| 10,238,420 B2 | 3/2019 | Karve et al. |
| 10,245,010 B2 | 4/2019 | Miller et al. |
| 10,251,812 B2 | 4/2019 | Tomes et al. |
| 10,258,783 B2 | 4/2019 | Miller et al. |
| 10,314,629 B2 | 6/2019 | Park et al. |
| 10,405,938 B2 | 9/2019 | Ramsey |
| 10,441,454 B2 | 10/2019 | Tanghoej et al. |
| 10,456,149 B2 | 10/2019 | Miller |
| 10,456,497 B2 | 10/2019 | Howell et al. |
| 10,595,896 B2 | 3/2020 | Miller |
| 10,722,247 B2 | 7/2020 | Browne et al. |
| 10,893,887 B2 | 1/2021 | Blanchard |
| 2003/0060781 A1 | 3/2003 | Mogensen et al. |
| 2003/0225344 A1 | 12/2003 | Miller |
| 2003/0225411 A1 | 12/2003 | Miller |
| 2003/0229308 A1 | 12/2003 | Tsals et al. |
| 2004/0162559 A1* | 8/2004 | Arramon ............ A61B 17/3417 606/62 |
| 2004/0220497 A1 | 11/2004 | Findlay et al. |
| 2004/0243135 A1 | 12/2004 | Koseki |
| 2005/0033235 A1 | 2/2005 | Flint |
| 2005/0035014 A1 | 2/2005 | Cane |
| 2005/0101912 A1 | 5/2005 | Faust et al. |
| 2005/0113866 A1 | 5/2005 | Heinz et al. |
| 2005/0148940 A1 | 7/2005 | Miller |
| 2005/0165403 A1 | 7/2005 | Miller |
| 2005/0261693 A1 | 11/2005 | Miller et al. |
| 2006/0015066 A1 | 1/2006 | Turieo et al. |
| 2006/0025723 A1 | 2/2006 | Ballarini |
| 2007/0010843 A1* | 1/2007 | Green ................ A61B 17/3421 606/167 |
| 2007/0016138 A1 | 1/2007 | Swisher et al. |
| 2007/0049945 A1 | 3/2007 | Miller |
| 2007/0191772 A1 | 8/2007 | Wojcik |
| 2007/0270775 A1 | 11/2007 | Miller et al. |
| 2008/0086142 A1* | 4/2008 | Kohm ................ A61B 17/3472 606/92 |
| 2008/0119759 A1 | 5/2008 | McLain |
| 2008/0119821 A1* | 5/2008 | Agnihotri .......... A61B 17/8819 604/513 |
| 2008/0140014 A1 | 6/2008 | Miller et al. |
| 2008/0154304 A1 | 6/2008 | Crawford et al. |
| 2008/0208136 A1 | 8/2008 | Findlay et al. |
| 2008/0215056 A1 | 9/2008 | Miller et al. |
| 2008/0221580 A1 | 9/2008 | Miller et al. |
| 2008/0257359 A1 | 10/2008 | Rumsey |
| 2009/0048575 A1 | 2/2009 | Waters |
| 2009/0054808 A1 | 2/2009 | Miller |
| 2009/0093830 A1 | 4/2009 | Miller |
| 2009/0105775 A1 | 4/2009 | Mitchell et al. |
| 2009/0118639 A1 | 5/2009 | Moos et al. |
| 2009/0204024 A1 | 8/2009 | Miller |
| 2009/0228014 A1 | 9/2009 | Stearns et al. |
| 2009/0306697 A1 | 12/2009 | Fischvogt |
| 2010/0030105 A1 | 2/2010 | Noishiki et al. |
| 2010/0082033 A1* | 4/2010 | Germain ............ A61B 17/3472 606/86 R |
| 2010/0152616 A1 | 6/2010 | Beyhan et al. |
| 2010/0185161 A1* | 7/2010 | Pellegrino .......... A61B 17/3421 604/272 |
| 2010/0204649 A1 | 8/2010 | Miller et al. |
| 2010/0280410 A1 | 11/2010 | Moos et al. |
| 2010/0286607 A1 | 11/2010 | Saltzstein |
| 2010/0298830 A1 | 11/2010 | Browne et al. |
| 2010/0298831 A1 | 11/2010 | Browne et al. |
| 2010/0312246 A1 | 12/2010 | Browne et al. |
| 2011/0004163 A1 | 1/2011 | Vaidya |
| 2011/0028976 A1 | 2/2011 | Miller |
| 2011/0137253 A1 | 6/2011 | Simonton et al. |
| 2012/0041454 A1 | 2/2012 | Johnstone |
| 2012/0202180 A1 | 8/2012 | Stock et al. |
| 2012/0203154 A1 | 8/2012 | Tzachar |

(56) References Cited

U.S. PATENT DOCUMENTS

| | | |
|---|---|---|
| 2013/0030439 A1 | 1/2013 | Browne et al. |
| 2013/0041345 A1 | 2/2013 | Kilcoin et al. |
| 2013/0072938 A1 | 3/2013 | Browne et al. |
| 2013/0079720 A1 | 3/2013 | Finnestad et al. |
| 2013/0102924 A1 | 4/2013 | Findlay et al. |
| 2013/0158484 A1 | 6/2013 | Browne et al. |
| 2013/0178807 A1 | 7/2013 | Baid |
| 2013/0331840 A1 | 12/2013 | Teisen et al. |
| 2014/0039400 A1 | 2/2014 | Browne et al. |
| 2014/0046327 A1 | 2/2014 | Tzachar et al. |
| 2014/0074102 A1 | 3/2014 | Mandeen et al. |
| 2014/0081281 A1 | 3/2014 | Felder |
| 2014/0142577 A1 | 5/2014 | Miller |
| 2014/0262408 A1 | 9/2014 | Woodard |
| 2014/0262880 A1 | 9/2014 | Yoon |
| 2014/0276205 A1 | 9/2014 | Miller et al. |
| 2014/0276206 A1 | 9/2014 | Woodward et al. |
| 2014/0276366 A1 | 9/2014 | Bourne et al. |
| 2014/0276471 A1 | 9/2014 | Emery et al. |
| 2014/0276833 A1 | 9/2014 | Larsen et al. |
| 2014/0276839 A1 | 9/2014 | Forman et al. |
| 2014/0276927 A1* | 9/2014 | Barker .............. A61M 25/0668 606/129 |
| 2014/0343454 A1 | 11/2014 | Miller et al. |
| 2014/0343497 A1 | 11/2014 | Baid |
| 2015/0011941 A1 | 1/2015 | Saeki |
| 2015/0126931 A1 | 5/2015 | Holm et al. |
| 2015/0127006 A1 | 5/2015 | Miller |
| 2015/0196737 A1 | 7/2015 | Baid |
| 2015/0223786 A1 | 8/2015 | Morgan et al. |
| 2015/0230823 A1 | 8/2015 | Morgan et al. |
| 2015/0238733 A1 | 8/2015 | bin Abdulla |
| 2015/0342615 A1 | 12/2015 | Keinan et al. |
| 2015/0342756 A1 | 12/2015 | Bays et al. |
| 2015/0351797 A1 | 12/2015 | Miller et al. |
| 2015/0366569 A1 | 12/2015 | Miller |
| 2016/0022282 A1 | 1/2016 | Miller et al. |
| 2016/0058432 A1 | 3/2016 | Miller |
| 2016/0066954 A1 | 3/2016 | Miller et al. |
| 2016/0106441 A1 | 4/2016 | Teisen et al. |
| 2016/0136410 A1 | 5/2016 | Aklog et al. |
| 2016/0183974 A1 | 6/2016 | Miller |
| 2016/0228676 A1 | 8/2016 | Glithero et al. |
| 2016/0235949 A1 | 8/2016 | Baid |
| 2016/0354539 A1 | 12/2016 | Tan et al. |
| 2016/0361519 A1 | 12/2016 | Teoh et al. |
| 2017/0021138 A1 | 1/2017 | Sokolski |
| 2017/0043135 A1 | 2/2017 | Knutsson |
| 2017/0056122 A1 | 3/2017 | Ramsey |
| 2017/0105763 A1 | 4/2017 | Karve et al. |
| 2017/0136217 A1 | 5/2017 | Riesenberger et al. |
| 2017/0143395 A1 | 5/2017 | Park et al. |
| 2017/0151419 A1 | 6/2017 | Sonksen |
| 2017/0156740 A9 | 6/2017 | Stark |
| 2017/0156751 A1 | 6/2017 | Csernatoni |
| 2017/0209129 A1 | 7/2017 | Fagundes et al. |
| 2017/0303962 A1 | 10/2017 | Browne et al. |
| 2017/0303963 A1 | 10/2017 | Kilcoin et al. |
| 2018/0092662 A1 | 4/2018 | Rioux et al. |
| 2018/0116642 A1 | 5/2018 | Woodard et al. |
| 2018/0116693 A1 | 5/2018 | Blanchard et al. |
| 2018/0117262 A1 | 5/2018 | Islam |
| 2018/0125465 A1 | 5/2018 | Muse et al. |
| 2018/0154112 A1 | 6/2018 | Chan et al. |
| 2018/0206933 A1 | 7/2018 | Healey et al. |
| 2018/0221564 A1 | 8/2018 | Patel et al. |
| 2018/0236182 A1 | 8/2018 | Charlebois et al. |
| 2018/0256209 A1 | 9/2018 | Muse et al. |
| 2019/0021807 A1 | 1/2019 | Barnell et al. |
| 2019/0060607 A1 | 2/2019 | Yabu et al. |
| 2019/0076132 A1 | 3/2019 | Tzachar et al. |
| 2019/0125404 A1 | 5/2019 | Shippert |
| 2019/0150953 A1 | 5/2019 | Budyansky et al. |
| 2019/0151606 A1 | 5/2019 | Mottola et al. |
| 2019/0201053 A1 | 7/2019 | Ben Mocha et al. |
| 2019/0282244 A1 | 9/2019 | Muse |
| 2019/0328370 A1 | 10/2019 | Muse |
| 2019/0343556 A1 | 11/2019 | Coppedge et al. |
| 2021/0093358 A1 | 4/2021 | Lindekugel et al. |
| 2021/0137558 A1 | 5/2021 | Lindekugel |
| 2024/0050126 A1 | 2/2024 | Blanchard |

FOREIGN PATENT DOCUMENTS

| | | |
|---|---|---|
| WO | 1997024151 A1 | 7/1997 |
| WO | 1998052638 A3 | 2/1999 |
| WO | 2004000408 A1 | 12/2003 |
| WO | 2004073500 A2 | 9/2004 |
| WO | 2005/046769 A2 | 5/2005 |
| WO | 05041790 A2 | 5/2005 |
| WO | 2005053506 A2 | 6/2005 |
| WO | 2005072625 A2 | 8/2005 |
| WO | 2006/047737 A2 | 5/2006 |
| WO | 2007018809 A2 | 2/2007 |
| WO | 2008002961 A2 | 1/2008 |
| WO | 2008016757 A2 | 2/2008 |
| WO | 2008033871 A2 | 3/2008 |
| WO | 2008033872 A2 | 3/2008 |
| WO | 2008033873 A2 | 3/2008 |
| WO | 2008033874 A2 | 3/2008 |
| WO | 2008054894 A2 | 5/2008 |
| WO | 2008086258 A1 | 7/2008 |
| WO | 2008124206 A2 | 10/2008 |
| WO | 2008124463 A2 | 10/2008 |
| WO | 2008130893 A1 | 10/2008 |
| WO | 2008134355 A2 | 11/2008 |
| WO | 2008144379 A2 | 11/2008 |
| WO | 2009070896 A1 | 6/2009 |
| WO | 2010043043 A2 | 4/2010 |
| WO | 2011097311 A2 | 8/2011 |
| WO | 2011139294 A1 | 11/2011 |
| WO | 2013009901 A2 | 1/2013 |
| WO | 2013173360 A1 | 11/2013 |
| WO | 2014142948 A1 | 9/2014 |
| WO | 2014144239 A1 | 9/2014 |
| WO | 2014144262 A1 | 9/2014 |
| WO | 2014144489 A2 | 9/2014 |
| WO | 2014144757 A1 | 9/2014 |
| WO | 2014144797 A1 | 9/2014 |
| WO | 2015/177612 A1 | 11/2015 |
| WO | 2016033016 A1 | 3/2016 |
| WO | 16053834 A1 | 4/2016 |
| WO | 2016163939 A1 | 10/2016 |
| WO | 18006045 A1 | 1/2018 |
| WO | 2018025094 A1 | 2/2018 |
| WO | 2018058036 A1 | 3/2018 |
| WO | 2018075694 A1 | 4/2018 |
| WO | 18098086 A1 | 5/2018 |
| WO | 2018165334 A1 | 9/2018 |
| WO | 2018165339 A1 | 9/2018 |
| WO | 2019051343 A1 | 3/2019 |
| WO | 2019051412 A1 | 3/2019 |
| WO | 2019164990 A1 | 8/2019 |
| WO | 2019215705 A1 | 11/2019 |
| WO | 2020/012051 A1 | 1/2020 |
| WO | 2021/062215 A1 | 4/2021 |
| WO | 2021173649 A1 | 9/2021 |

OTHER PUBLICATIONS

EP 17864208.8 filed May 24, 2019 Extended European Search Report filed May 19, 2020.

PCT/US17/57270 filed Oct. 18, 2017 International Search Report and Written Opinion dated Jan. 12, 2018.

PCT/US2017/058863 filed Oct. 27, 2017 International Search Report and Written Opinion dated Jan. 29, 2018.

PCT/US2018/021398 filed Mar. 7, 2018 International search report and written opinion dated May 21, 2018.

PCT/US2020/052809 filed Sep. 25, 2020 International Search Report and Written Opinion dated Jan. 5, 2021.

PCT/US2021/042040 filed Jul. 16, 2021 International Search Report and Written Opinion dated Oct. 4, 2021.

(56) References Cited

OTHER PUBLICATIONS

U.S. Appl. No. 15/796,471, filed Oct. 27, 2017 Advisory Action dated Jun. 15, 2020.
U.S. Appl. No. 15/796,471, filed Oct. 27, 2017 Final Office Action dated Apr. 23, 2020.
U.S. Appl. No. 15/796,471, filed Oct. 27, 2017 Non-Final Office Action dated Oct. 30, 2019.
U.S. Appl. No. 15/796,471, filed Oct. 27, 2017 Notice of Allowance dated Jun. 15, 2020.
U.S. Appl. No. 15/796,471, filed Oct. 27, 2017 Restriction Requirement dated Jul. 8, 2019.
U.S. Appl. No. 17/033,093, filed Sep. 25, 2020 Restriction Requirement dated Nov. 15, 2022.
U.S. Appl. No. 17/033,093, filed Sep. 25, 2020 Non-Final Office Action dated Mar. 2, 2023.
U.S. Appl. No. 17/152,509, filed Jan. 19, 2021 Non-Final Office Action dated May 4, 2023.
EP 20868558.6 filed Apr. 21, 2022 Extended European Search Report dated Aug. 11, 2023.
PCT/US2021/019388 filed Feb. 24, 2021 International Search Report and Written Opinion dated May 17, 2021.
U.S. Appl. No. 17/033,093, filed Sep. 25, 2020 Advisory Action dated Oct. 4, 2023.
U.S. Appl. No. 17/033,093, filed Sep. 25, 2020 Final Office Action dated Sep. 8, 2023.
U.S. Appl. No. 17/033,093, filed Sep. 25, 2020 Non-Final Office Action dated Nov. 8, 2023.
U.S. Appl. No. 17/152,509, filed Jan. 19, 2021 Notice of Allowance dated Sep. 7, 2023.
U.S. Appl. No. 17/033,093, filed Sep. 25, 2020 Final Office Action dated Feb. 15, 2024.
U.S. Appl. No. 17/033,093, filed Sep. 25, 2020 Notice of Allowance dated Apr. 30, 2024.
U.S. Appl. No. 17/378,304, filed Jul. 16, 2021 Non-Final Office Action dated Jun. 5, 2024.

\* cited by examiner

FLEXIBLE INTRAOSSEOUS OBTURATOR

PRIORITY

This application claims the benefit of priority to U.S. Provisional Application No. 62/983,434, filed Feb. 28, 2020, which is incorporated by reference in its entirety into this application.

SUMMARY

Current intraosseous access devices include rigid, stainless steel obturators to prevent bone fragments and other tissues from blocking the needle lumen during a placement event. Obturators in intraosseous ("I.O.") needles prevent a hollow needle from coring the bone as it is drilled through the bone. The obturator is disposed within the needle lumen and extends flush with the needle bevel. This blocks the inner lumen of the needle and prevents the needle from becoming blocked by bone fragments as it is drilled through the bone.

While stainless steel obturators are not intentionally provided with a distal cutting edge, the tip of the obturator is ground flush with the bevel of the needle to prevent any pockets forming that might collect bone fragments and the like. As shown for example, in FIGS. 1A-1C, this results in a sharpened tip 146 that requires a tip safety mechanism 105 to prevent accidental needle stick injuries once removed from the needle 204. Further the stainless steel obturator requires a concentric groove, or recess 150, to allow the tip safety mechanism to lock on to the tip of the obturator 104. This requires added complexity and cost in manufacturing intraosseous access devices that include safety shields and structures to engage the shields.

Briefly summarized, embodiments disclosed herein are directed to apparatus and methods for a flexible obturator for use with an intraosseous device, which resolves the previously stated problems. Disclosed herein is an access assembly for use with an intraosseous access device including, a needle including a rounded distal region communicating with a beveled distal opening, and an obturator formed of a flexible material, the obturator including a radially symmetrical elongate body designed for insertion in a lumen of the needle.

In some embodiments the elongate body is deformable when disposed in the lumen of the needle to conform to an inner profile of the lumen. The obturator comprises a distal surface extending perpendicular to a longitudinal axis. The obturator comprises a curved distal surface. In some embodiments the elongate body further includes a beveled distal surface configured to align with the beveled distal opening of the needle. The flexible material displays relatively low columnar strength, low shear strength and high compressive strength. The flexible material includes one of a plastic, polymer, thermoplastic, Polytetrafluoroethylene ("PTFE"), Polyethylene ("PE"), Polyurethane ("PU"), rubber, silicone, metal, alloy, or Nitinol.

In some embodiments the elongate body further includes a needle hub configured to support the needle and define a hub lumen that communicates with the needle lumen, and an obturator hub configured to support the obturator, wherein a distal tip of the obturator extends through the needle lumen and extends distally of a distal tip of the needle when the obturator hub engages the needle hub. In some embodiments the elongate body further includes a lumen clearing mechanism, configured to advance the obturator relative to the needle lumen to clear material from a distal portion of the needle lumen. The lumen clearing mechanism is automatically triggered when the obturator is removed from the needle lumen.

Also disclosed is a method of manufacturing an access assembly including, providing a needle supported by a needle hub and defining a lumen, providing an obturator supported by an obturator hub, advancing the obturator through the needle lumen until a distal tip extends distally of a distal tip of the needle, trimming a distal portion of the obturator to provide a distal surface that is flush with a beveled distal surface of the needle.

In some embodiments, the obturator hub engages the needle hub when the distal tip of the obturator extends distally of the distal tip of the needle. In some embodiments the method further includes adhering the obturator to the obturator hub prior to advancing the obturator through the needle lumen. The obturator is formed of a flexible material that displays relatively low columnar strength, low shear strength and high compressive strength. The flexible material includes one of a plastic, polymer, thermoplastic, Polytetrafluoroethylene ("PTFE"), Polyethylene ("PE"), Polyurethane ("PU"), rubber, silicone, metal, alloy, or Nitinol. The obturator defines a radially symmetrical elongate body. Providing an obturator includes the obturator defining a distal surface extending perpendicular to a longitudinal axis of the obturator. Providing an obturator includes the obturator defining a radially symmetrical curved distal surface. In some embodiments the method further includes a lumen clearing mechanism, configured to advance the obturator relative to the needle lumen to clear material from a distal portion of the needle lumen. The lumen clearing mechanism is automatically triggered when the obturator hub is detached from the needle hub.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal end portion, or the proximal length of the needle can include the proximal end of the needle; however, the proximal portion, the proximal end portion, or the proximal length of the needle need not include the proximal end of the needle. That is, unless context suggests otherwise, the proximal portion, the proximal end portion, or the proximal length of the needle is not a terminal portion or terminal length of the needle.

With respect to "distal," a "distal portion" or a "distal end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal end portion, or the distal length of the needle can include the distal end of the needle; however, the distal portion, the distal end portion, or the distal length of the needle need not include the distal end of the needle. That is, unless context suggests otherwise, the distal portion, the distal end portion, or the distal length of the needle is not a terminal portion or terminal length of the needle.

Figure 1A:
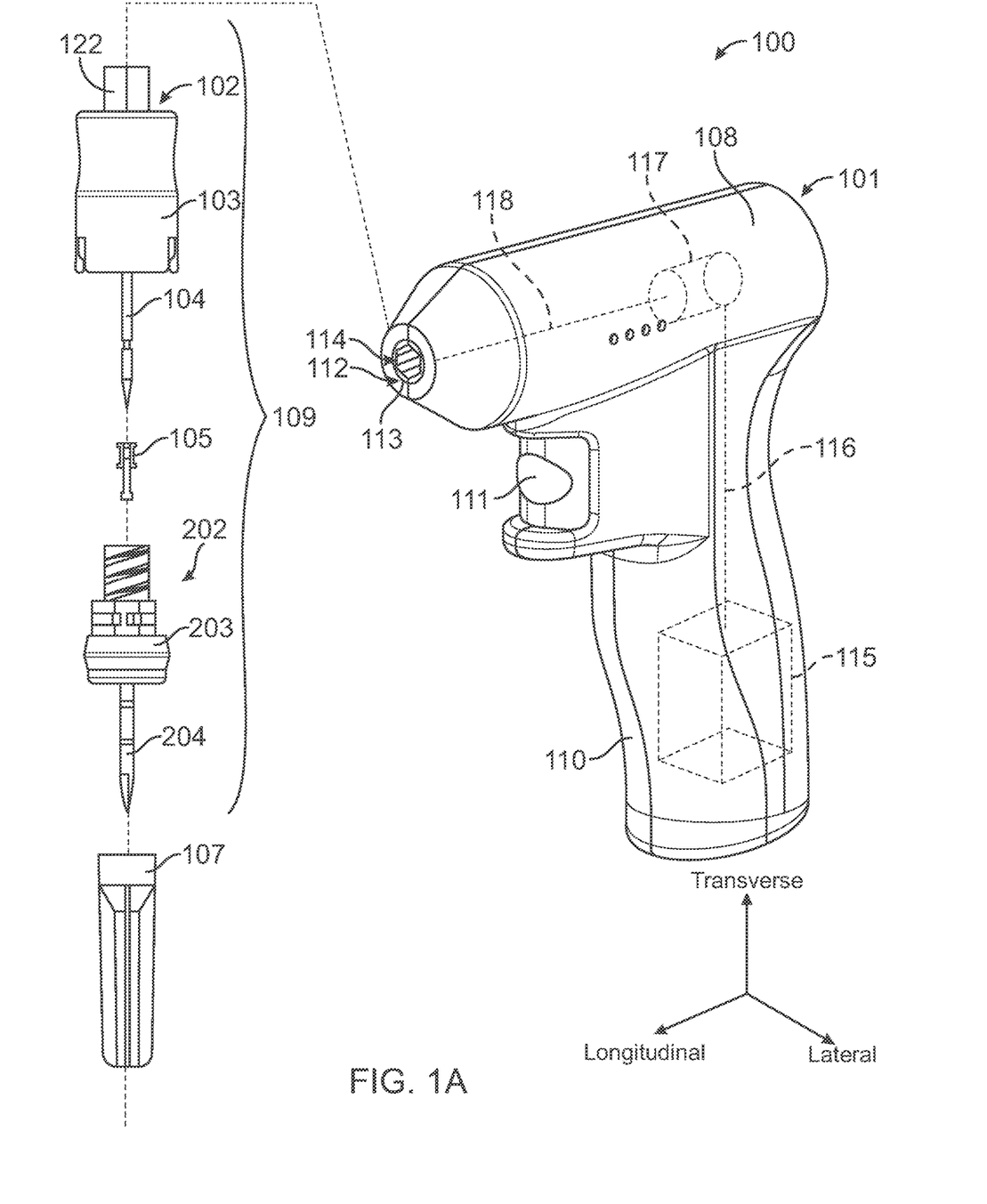
FIG. 1A illustrates an exploded view of an exemplary intraosseous access system, wherein an access assembly subset of the system is depicted slightly enlarged and in elevation, and a driver component is depicted in perspective, in accordance with embodiments disclosed herein.

As shown in FIG. 1A, and to assist in the description of embodiments described herein, a longitudinal axis extends substantially parallel to an axial length of a needle 204 extending from the driver 101. A lateral axis extends normal to the longitudinal axis, and a transverse axis extends normal to both the longitudinal and lateral axes. Unless defined otherwise, all technical and scientific terms used herein have the same meaning as commonly understood by those of ordinary skill in the art.

The present disclosure generally relates to intraosseous ("IO") access devices, systems, and methods thereof. FIG. 1A shows an exploded view of an exemplary intraosseous access system 100, with some components thereof shown in elevation and another shown in perspective. The intraosseous access system 100 can be used to penetrate skin and underlying hard bone for intraosseous access, such as, for example to access the marrow of the bone and/or a vasculature of the patient via a pathway through an interior of the bone.

In an embodiment, the system includes a driver 101 and an access assembly 109. The driver 101 can be used to rotate the access assembly 109 into a bone of a patient. In embodiments, the driver 101 can be automated or manual. In an embodiment, the driver 101 is an automated driver 108. For example, the automated driver 108 can be a drill that achieves high rotational speeds. The intraosseous access system 100 can further include an obturator assembly 102, a shield 105, and a needle assembly 202, which may be referred to, collectively, as the access assembly 109. In an embodiment, the obturator assembly 102 includes an obturator 104 and an obturator hub 103. In an embodiment, the obturator hub 103 is attached to the obturator 104 in any suitable manner (e.g., one or more adhesives or overmolding). The obturator hub 103 can be configured to interface with the driver 101.

In an embodiment, the shield 105 is configured to couple with the obturator 104. The coupling can allow longitudinal movement between the obturator 104 and the shield 105, when the shield 105 is in a first operational mode. In a second operational mode, the longitudinal movement between the obturator 104 and the shield 105 can be prevent.

For example, in the first operational mode, the obturator 104 maintains the shield 105 in an unlocked state. The obturator 104 can then be moved to a position where the shield 105 is no longer maintained in the unlocked state, and the shield 105 may automatically transition to the second operational mode, i.e. a locked state, in which little or no longitudinal movement is permitted between the shield 105 and the obturator 104. In the second operational mode, the shield 105 can inhibit inadvertent contact with a distal tip of the obturator 104 and prevent accidental needle stick injuries. In an embodiment, the shield 105 may be configured to rotate relative to the obturator 104, about a longitudinal axis, one of the first operational mode or the second operational mode.

The automated driver 108 may take any suitable form. The driver 108 may include a handle 110 that may be gripped by a single hand of a user. The driver 108 may further include an actuator 111, e.g. trigger actuator, of any suitable variety via which a user may selectively actuate the driver 108 to effect rotation of a coupling interface 112. For example, the actuator 111 may comprise a button, as shown, or a switch or other mechanical or electrical element for actuating the driver 108. In an embodiment, the coupling interface 112 is formed as a socket 113 that defines a cavity 114. The coupling interface 112 can be configured to couple with the obturator hub 103. In an embodiment, the socket 113 includes sidewalls that substantially define a hexagonal cavity into which a hexagonal protrusion of the obturator hub 103 can be received. Other suitable connection interfaces are contemplated.

The automated driver 108 can include an energy source 115 of any suitable variety that is configured to energize the rotational movement of the coupling interface 112. For example, in some embodiments, the energy source 115 may comprise one or more batteries that provide electrical power for the automated driver 108. In other embodiments, the energy source 115 can comprise one or more springs (e.g., a coiled spring) or other biasing member that may store potential mechanical energy that may be released upon actuation of the actuator 111. The energy source 115 may be coupled with the coupling interface 112 in any suitable manner. For example, in an embodiment, the automated driver 108 includes an electrical, mechanical, or electromechanical coupling 116 to a gear assembly 117. In some embodiments, the coupling 116 may include an electrical motor that generates mechanical movement from electrical energy provided by an electrical energy source 115. In other embodiments, the coupling 116 may include a mechanical linkage that mechanically transfers rotational energy from a mechanical (e.g., spring-based) energy source 115 to the gear assembly 117. The automated driver 108 can include a mechanical coupling 118 of any suitable variety to couple the gear assembly 117 with the coupling interface 112. In other embodiments, the gear assembly 117 may be omitted.

In embodiments, the automated driver 108 can rotate the coupling interface 112, and thereby, can rotate the access assembly 109 at rotational speeds significantly greater than can be achieved by manual rotation of the access assembly 109. For example, in various embodiments, the automated driver 108 can rotate the access assembly 109 at speeds of between 200 and 3,000 rotations per minute (rpm). However, it will be appreciated that lesser or greater rotational speeds are also contemplated.

Figure 1B:
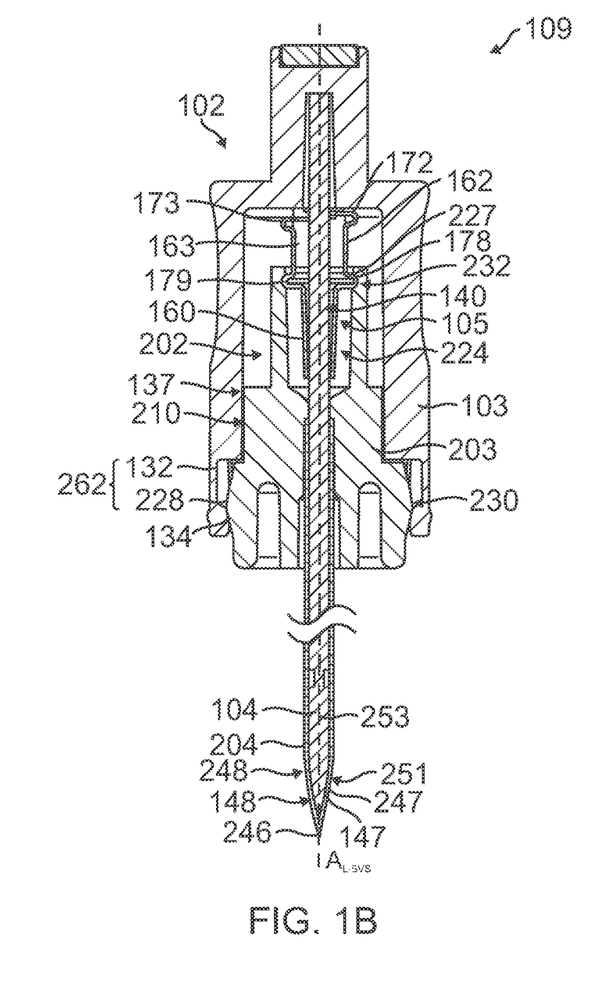
FIG. 1B illustrates a cross-sectional view of the access assembly of FIG. 1A, in accordance with embodiments disclosed herein.
Figure 1C:
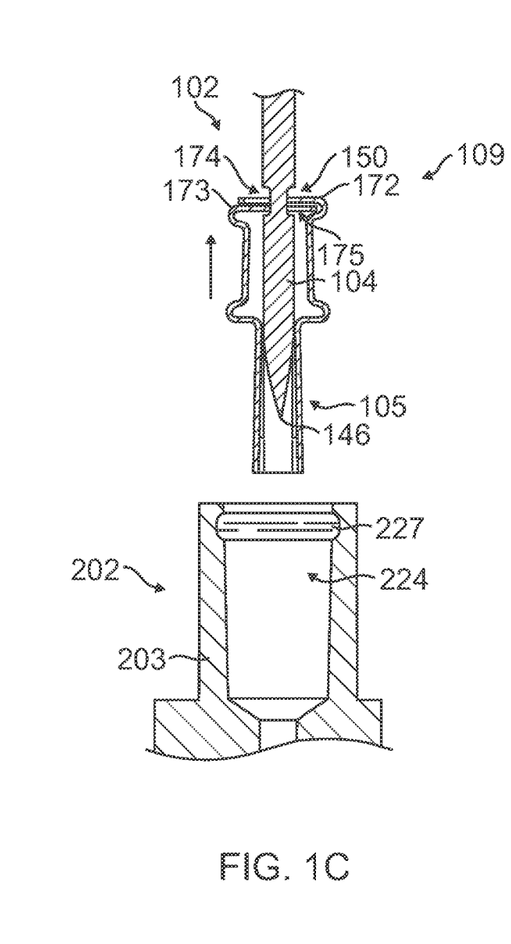
FIG. 1C illustrates a cross-sectional view of the obturator tip and safety shield removed from the access assembly of FIG. 1A, in accordance with embodiments disclosed herein.
Figure 1D:
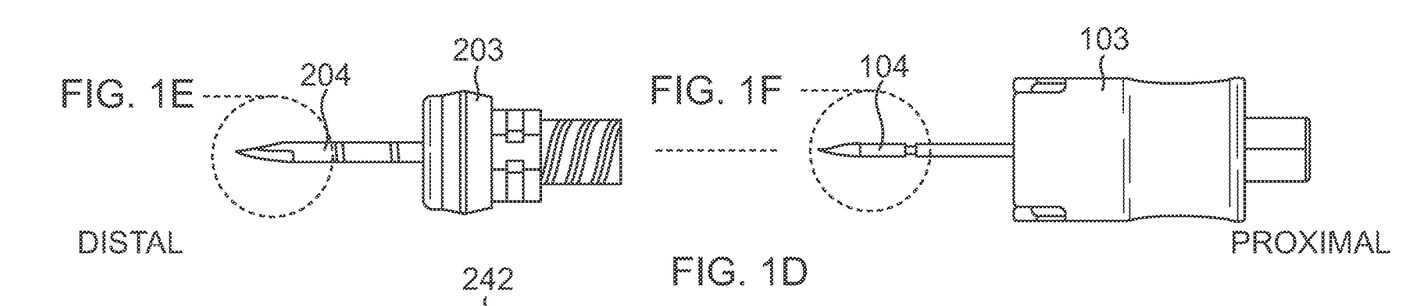
FIGS. 1D-1F illustrate close up detailed views of the access assembly of FIG. 1A, in accordance with embodiments disclosed herein.
Figure 1E:
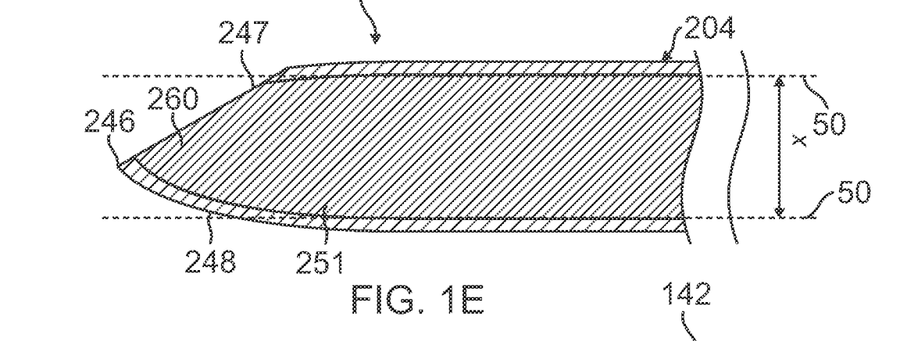
Figure 1F:
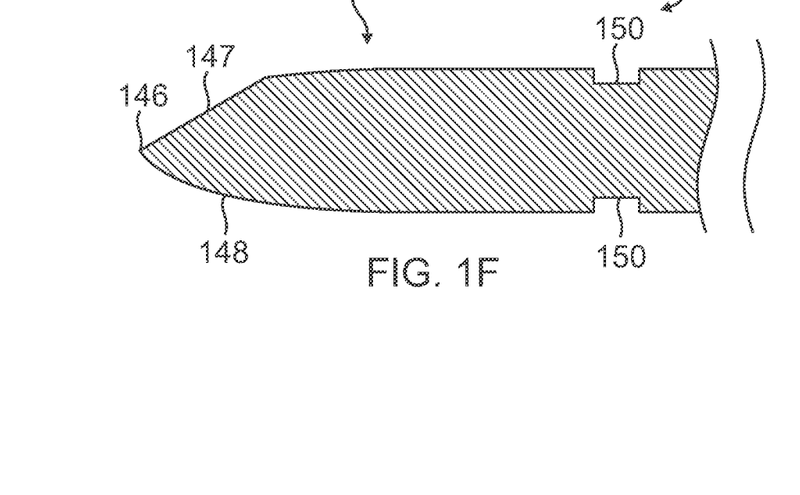

As shown in FIG. 1A, the needle assembly 202 includes a needle 204 and a needle hub 203 that is attached to the needle 204 in any suitable manner. The needle hub 203 can be configured to couple with the obturator hub 103 and may thereby be coupled with the driver 101. FIGS. 1B-1F show further details of the access assembly 109. FIG. 1B shows a cross-sectional view of the access assembly 109 with the needle hub 203 retained by the obturator hub 103. The obturator 104 is disposed within the needle and the shield 105 is in the unlocked position within the access assembly 109. FIG. 1C shows a cross-sectional view of the access assembly 109 with the obturator 104 removed from the needle and the shield in the second, locked operational mode. FIG. 1D shows an exploded view of the access assembly 109. FIG. 1E shows a close up, cross-sectional view of the needle 204. FIG. 1F shows a close up, cross-sectional view of the obturator 104.

As discussed herein, the obturator 104 is formed of a rigid material, e.g. stainless steel, to inhibit tissue and/or bone from entering a lumen of the needle 204 during an access event. Although not intentionally provided with a cutting distal edge, the rigid obturator 104 is ground flush with the beveled opening of the needle to provide a flush surface. Further the rigid material sufficiently rigid and strong to inhibit tissue and/or bone from entering a lumen of the needle 204 during an access event. As such, the obturator tip 146 is sufficiently sharpened to provide a risk of needle stick injuries, and the shield 105 is provided to engage the obturator 104, and prevent accidental needle stick injuries. Further details and embodiments of the intraosseous access system 100 can be found in WO 2018/075694, WO 2018/165334, WO 2018/165339, and US 2018/0116693, each of which is incorporated by reference in its entirety into this application.

FIG. 1B depicts an early stage of an illustrative method of using the intraosseous access system 100, and is a cross-sectional view of the access assembly 109 in an assembled state with an exemplary tip protection device. It should be appreciated that other means of tip protection are also contemplated and within the scope of the invention. The access assembly 109 includes the obturator assembly 102, the shield 105, and the needle assembly 202. In some instances, the access assembly 109 will be preassembled, and thus may be removed from any suitable sterile packaging substantially in the configuration depicted in FIG. 1B. In the illustrated assembled state, the keyed coupling interfaces 137, 210 of the obturator hub 103 and the needle hub 203, respectively, can cooperate to ensure that a predetermined relationship between the obturator 104 and the needle 204 is achieved. Thus, the keyed coupling interfaces 137, 210 can ensure that the obturator 104 defines a fixed angular orientation relative to the needle 204. The coupling interfaces 137, 210 may likewise maintain the fixed angular orientation during rotation of the access assembly 109 during an insertion event, e.g., during rotation of the access assembly 109 via the automated driver 108.

The distal face 147 of the obturator 104 is slightly recessed relative to the distal face 247 of the needle 204. Additionally, the distal faces 147, 247 of the obturator 104 and the needle 204, respectively, are substantially parallel to each other. In some embodiments, the obturator 104 does not cut either through skin or bone during an insertion event. In other embodiments, the distal faces 147, 247 may be substantially flush with each other. The obturator 104 can substantially fill or otherwise block passage into the lumen 251 of the needle 204. For example, in the illustrated embodiment, the distal face 147 of the obturator 104 is substantially the same size as an opening into a distal end of the lumen 251. In various embodiments, an area of the distal face 147 of the obturator 104 is no greater than 5, 10, 15, or 20 percent smaller than an area defined by an inner edge of the distal face 247 of the needle 204. The obturator 104 can inhibit or prevent tissue and/or bone material from entering and/or progressing into the lumen 251 of the needle 204.

The interior surface 253 of the needle 204 and an exterior surface of the obturator 104 can be complementarily shaped and/or otherwise configured to prevent or inhibit ingress of tissue, bone, and/or other matter. In further embodiments, a fit between the obturator 104 and the needle 204 can permit the obturator 104 to be readily removed from needle 204. For example, a snug fit, a loose fit, or a minimal gap may be provided between at least a portion between the obturator 104 and the needle 204. During assembly of the access assembly 109, the arms or projections 132 of the obturator hub 103 can be advanced over the skirt 228 of the needle hub 203. The snap interface or inward protrusions 134 of the projections 132 can grip an underside of the skirt 228 to maintain the obturator hub 103 and the needle hub 203 in a coupled state. The skirt 228 is shaped substantially as an outward protrusion, and the inner surface of the arm 132 substantially defines a recess into which the protrusion is received. In other embodiments, the protrusion/recess interface may be reversed. For example, the arm 132 may define a protrusion is received into a recess defined by the skirt 228 to couple the obturator hub 103 with the needle hub 203.

The projection 132 and the skirt 228 may collectively be referred to as a releasable engagement mechanism 262. The releasable engagement mechanism 262 may be configured to keep the obturator hub 103 and the needle hub 203 coupled together during general manipulation of the access assembly 109, such as during removal from packaging and/or coupling thereof with the automated driver 108. The releasable engagement mechanism 262 may, however, provide a relatively weak coupling that is capable of being released upon application of sufficient removal force to the obturator hub 103 in a proximal direction, relative to the needle hub 203. For example, the releasable engagement mechanism 262 may provide a coupling force that tends to keep the obturator hub 103 engaged with the needle hub 203. When a proximally directed force on the obturator hub 103 exceeds the coupling force of the releasable engagement mechanism 262, the releasable engagement mechanism 262 can disengage and permit the obturator hub 103 to be withdrawn from the needle hub 203. In various embodiments, the coupling force (i.e., the force that counteracts a proximally directed force on the obturator hub 103) can be no greater than about 0.25, 0.5, 0.75, 1.0, 1.5, or 2.0 pounds.

In certain embodiments, the releasable engagement mechanism 262 provides a coupling force that is significantly lower than an embedding force between the needle 204 and a bone within which the needle 204 is inserted. The releasable engagement mechanism 262 can be configured to permit the obturator hub 103 to be decoupled from the needle hub 203, after the needle hub 203 has been introduced into the bone, by imparting a proximally directed force on the obturator hub 103 that is smaller in magnitude than a force imparted on the cannula 204 by the bone that maintains the cannula 204 positioned in the bone. Accordingly, in some embodiments, after introducing the access assembly 109 into the bone, a user may simply pull back, or proximally, on the obturator hub 103 with any amount of force that exceeds the coupling force of the releasable engagement mechanism 262, and the obturator hub 103 will automatically disengage from the needle hub 203. Further, the obturator hub 103 can be withdrawn from the needle hub 203 and the patient, and the needle 204 can remain in the bone. In some instances, the user can remove the obturator hub 103 from the needle hub 203 using a single hand after the access assembly 109 has been introduced into the bone. Other suitable arrangements of the releasable engagement mechanism 262 are contemplated.

When the access assembly 109 is in the assembled state, the shield 105 can be coupled with each of the obturator 104 and the needle hub 204 in an unlocked state, in which the arms 162, 163 are deflected outwardly away from the longitudinal axis. In particular, the proximal end 140 of the obturator 104, which can define a larger diameter than does the recess 150, can extend through an entirety of the shield 105. The proximal end 140 of the obturator 104 extends through the lateral extensions 172, 173 and the collar 160. This larger diameter region of the obturator 104 can maintain the shield 105 in the unlocked state to permit the obturator 104 to translate relative to the shield 105 in a proximal direction when the user desires to remove the obturator hub 103 from the needle hub 204.

When the shield 105 is in the unlocked state, the arms are deflected outwardly, which can seat or otherwise position the outward protrusions 178, 179 of the arms 162, 163 respectively within the groove 227 of the needle hub 203. The outward protrusions 178, 179 thus can cooperate with the groove 227 to maintain the shield 105 in a fixed longitudinal position relative to the needle hub 203 during the initial stages of withdrawal of the obturator 104 through the shield 105. In other embodiments, the groove 227 and the outward protrusions 178, 179 can be reversed. For example, in some embodiments, an inner surface of the needle hub 203 may define one or more inward protrusions, and the arms 162, 163 may define inward recesses into which the inward protrusions are received when the shield 105 is in the unlocked state (relative to the obturator 104) and in the coupled state relative to the needle hub 203.

FIG. 1C is another enlarged cross-sectional view of the access assembly 109 when the obturator 104 has been fully withdrawn from the needle hub 203. Prior to the depicted stage, the obturator 104 is withdrawn proximally by a sufficient amount to bring the recess 150 into the vicinity of the openings 174, 175. Due to the reduced diameter of the recess 150, the constricted portions of the openings 174, 175 fit into the recess 150 and the arms 162, 163 are thus permitted to automatically transition to their unbiased, non-deflected, or non-deformed state, i.e., the arms 162, 163 can resiliently return to a less bent or unbent state to automatically lock the shield 105 to the obturator 104.

When the shield 105 is in the locked state, portions of the lateral extensions 172, 173 that define the constricted portions of the openings 174, 175 enter into the recess 150 to secure the shield 105 to the obturator 104. When the shield 105 is locked to the obturator 104, movement of the shield 105 relative to the obturator 104 can be prevented or delimited in one or more directions (e.g., longitudinally and/or rotationally). In some embodiments, interference between the lateral extensions 172, 173 and proximal and distal faces of the recess 150, respectively, can delimit longitudinal movement of the shield 105 relative to the obturator 104. When the arms 162, 163 automatically transition to the locked state relative to the obturator 104, the arms 162, 163 substantially simultaneously decouple the shield from the needle hub 203. In particular, the inward movement of the arms 162, 163 causes the outward protrusions to exit the groove 227 of the needle hub 203. This frees the shield 105 to move relative to the needle hub 203, such as for proximal movement in the longitudinal direction to exit the lumen 224. The shield 105 naturally remains in the locked state relative to the obturator 104 and restricts access to the distal tip 146 of the obturator 104.

As shown in FIG. 1E, which is an enlarged view of the obturator 104 within the needle 204, the distal portion of the needle lumen 251 defines an asymmetrical shape including a rounded portion 248 and a beveled face 247 including an opening 260 that communicates with the needle lumen 251. As such, the obturator 104 formed of rigid material, which is shown in isolation in FIG. 1F, includes a distal portion 142 shaped to match the distal portion of the needle lumen 251. Further, the obturator 104 includes a longitudinal length to match the longitudinal length of the needle lumen 251 to align the shaped portion with the needle lumen 251. As such, different lengths of rigid obturators 104 must be produced to match different longitudinal lengths of needles 204 and requires a high degree of engineering accuracy to position the distal portions correctly when the access assembly 109 is assembled.

FIGS. 2A-2E show an exemplary embodiment of an obturator assembly 102 that includes an obturator 304 formed of a flexible material. The obturator 304 can define a substantially circular cross-section and includes a diameter sized to fit snugly within the inner diameter of the needle lumen 251. In an embodiment, a longitudinal length of the obturator 304 can be longer than the length of the obturator 104 that is used with needle 204. As such, when the obturator hub 103 engages the needle hub 203, for example as shown in FIG. 1B, a distal tip 346 of the obturator 304 extends distally of the distal tip 246 of the needle 204.

Figure 2A:
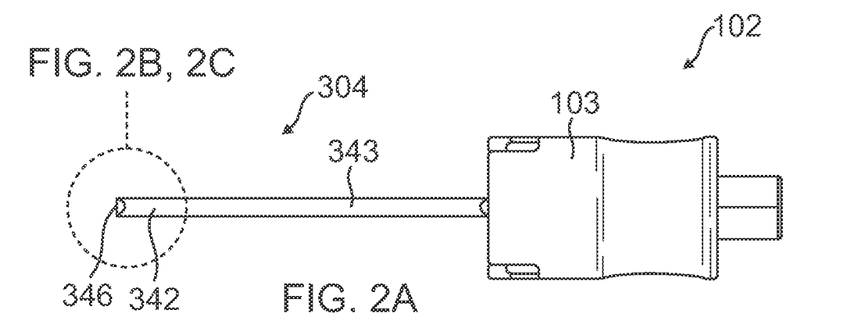
FIG. 2A illustrates an obturator assembly, in accordance with embodiments disclosed herein.
Figure 2B:
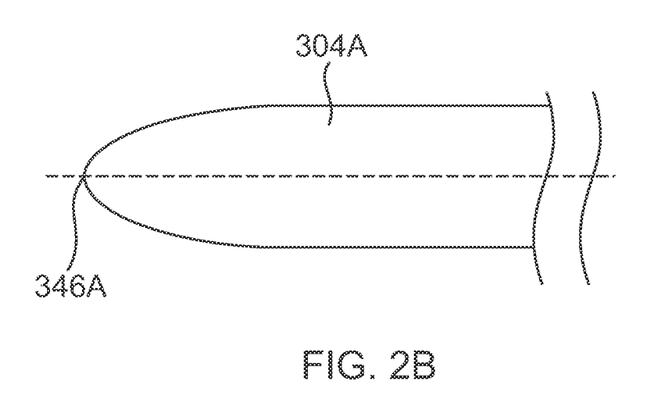
FIGS. 2B-2E illustrate side views and proximal end views of an obturator, in accordance with embodiments disclosed herein.
Figure 2C:
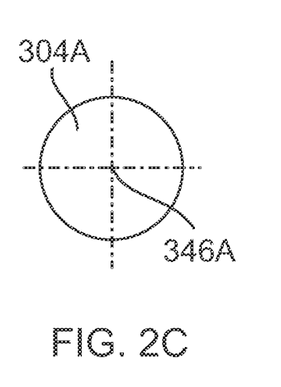
Figure 2D:
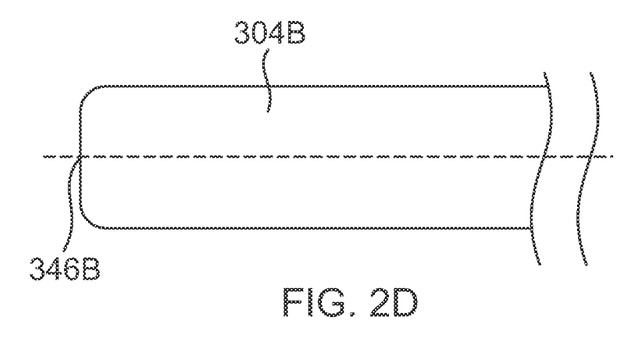
Figure 2E:
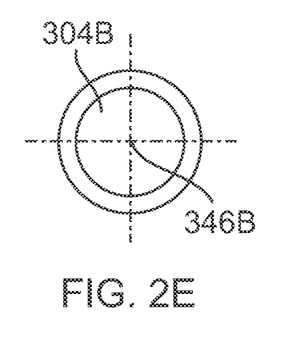

In an embodiment, as shown in FIG. 2B, the distal tip 346A of the obturator 304A can define a rounded tip. In an embodiment, as shown in FIG. 2D, the distal tip 346B of the obturator 304B can define a squared off tip that includes a distal surface extending perpendicular to the longitudinal axis. Optionally, the edges of the distal surface 346B can be rounded or chamfered. As shown in FIGS. 2C and 2E, in an embodiment, the obturator 304A, 304B, defines a radially symmetrical cross-section extending from the longitudinal axis.

In an embodiment, an obturator 304 can be formed of a flexible plastic that displays elastic properties and can readily deform or bend when a force is applied and return to an undeformed shape when the force is removed. In an embodiment, the obturator 304 can be formed of a material that displays a combination of mechanical properties including a relatively high flexibility, high elasticity, as well as a high compressive strength. In an embodiment, the obturator 304 can be formed of a plastic, polymer, thermoplastic, Polytetrafluoroethylene ("PTFE"), Polyethylene ("PE"), Polyurethane ("PU"), rubber, silicone, metal, alloy, Nitinol or similar material.

Figure 3A:
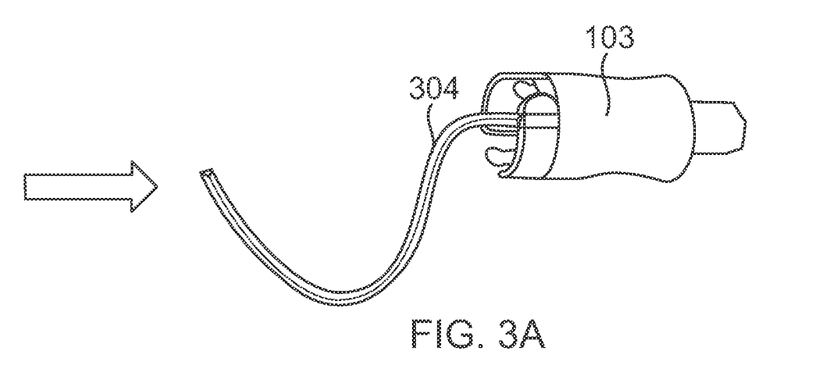
FIGS. 3A-3C illustrates an obturator assembly, in accordance with embodiments disclosed herein.
Figure 3B:
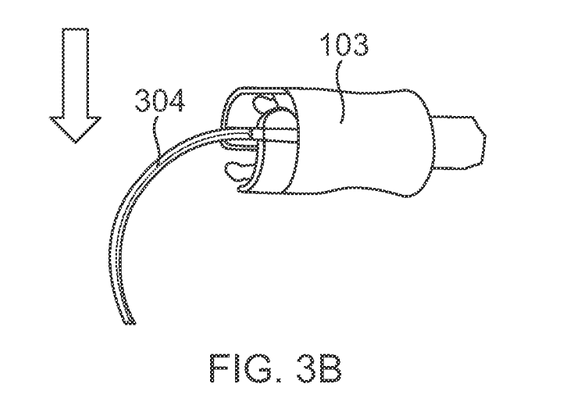
Figure 3C:
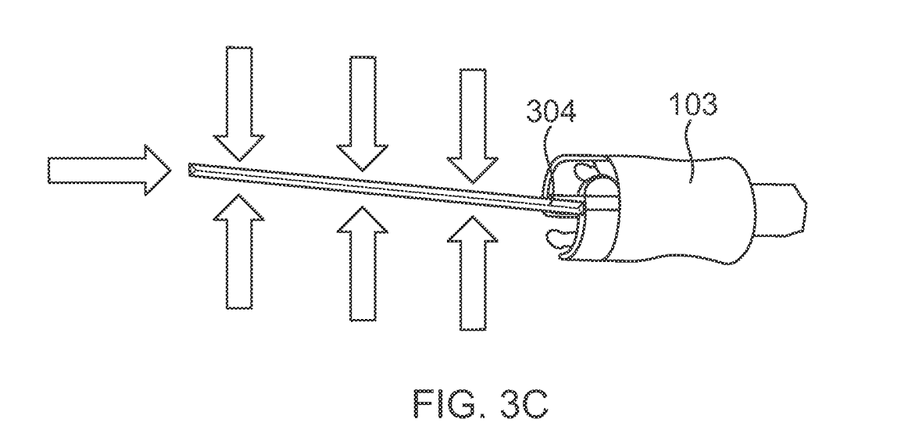

For example, as shown in FIG. 2A, the elongate obturator 304 extending from the obturator hub 103 is capable of self-supporting. However, as shown in FIG. 3A, when a longitudinal force is applied, the obturator 304 can flex and deform thereby displaying relatively low columnar strength. When the force is removed, the obturator 304 displays elastic properties and returns to its original shape. Further, as shown in FIG. 3B, when a lateral force is applied, the obturator 304 can flex and deform thereby displaying relatively low sheer strength. When the force is removed, the obturator 304 displays elastic properties and returns to its original shape. However, as shown in FIG. 3C, the obturator 304 can display a relatively high compressive strength such that the obturator 304 resists equal and opposite forces applied to the material with relatively little or no deformation.

Figure 3D:
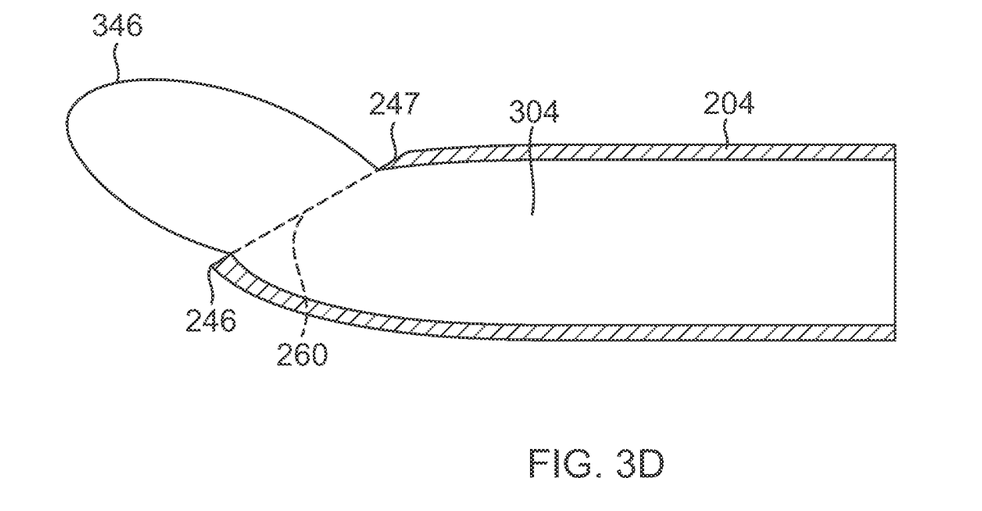
FIGS. 3D-3E illustrate a cross-sectional view of an obturator and needle assembly, in accordance with embodiments disclosed herein.
Figure 3E:
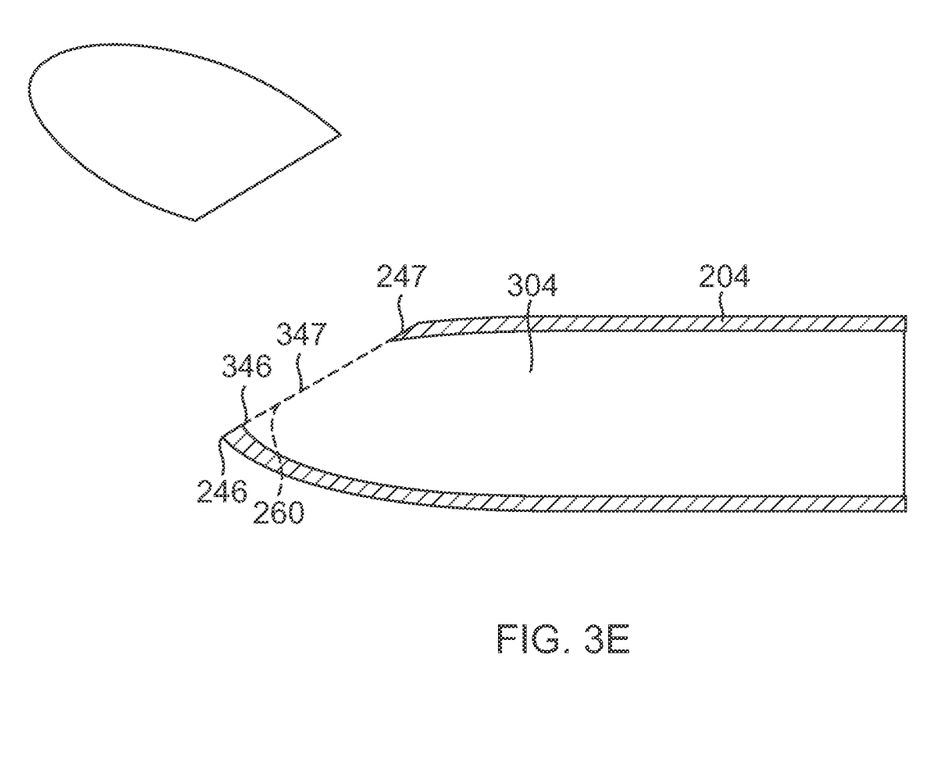

As shown in FIGS. 3D-3E, the flexible obturator 304 can advantageously conform to fit the shape of the distal portion of the needle lumen 251. Further, a distal portion 342 of the obturator 304 can flex to fit through the angled opening 260 such that a distal tip of the obturator 346 can extend distally of the distal tip 246 of the needle 204. As shown in FIG. 3E, the excess portion of the obturator 304 that extends through the opening 260, can be trimmed to provide a beveled surface 347 that lies flush with the beveled surface 247 of the needle 204. It will be appreciated that this provides a distal tip 346 that is then disposed proximally of the distal tip 246 of the needle.

It will be appreciated that the needle 204, formed of a rigid material, e.g. stainless steel, provides the necessary columnar strength and sheer strength to resist deformation of the needle 204/obturator 304 assembly. Further, the obturator 304, which is constrained within the needle lumen 251 displays sufficient compressive strength to resist a longitudinal force, e.g. to resist any bone fragments from being forced proximally into the needle lumen 251 during an insertion event. In an embodiment, the obturator 304 displays minimal compressive deformation that allows some retraction of the distal tip 346 into the needle lumen 251. In an embodiment, the elasticity of the obturator 304 then resumes the original, undeformed shape when the force is removed, i.e. when the needle penetrates the cortex layer of bone, and ejects any bone fragments or other material from the needle lumen 251.

Advantageously, due to the compressive strength of the obturator 304, the obturator 304 prevents bone material from entering the needle lumen during an insertion event. Further, when the obturator 304 is removed from needle 204, there is a reduced risk of needle stick injuries due to the flexible properties of the obturator 304. For example, when the flexible obturator 304, by itself, is subjected to longitudinal or lateral forces, the mechanical properties are configured or allow the obturator 304 to flex, preventing breakage of the skin. Similarly, although the tip 346 of the obturator presents a sharpened point, the mechanical properties are configured allow the obturator 304 to deform, preventing breakage of the skin.

An exemplary method of manufacturing an access assembly 109, using the flexible obturator 304, is provided. An elongate cylinder of flexible material is provided to form a body 343 of the obturator 304 and defines a circular cross sectional shape. The outer diameter of the body 343 of the obturator 304 is configured to fit tightly within an inner diameter of the needle lumen 251. A proximal end of the obturator body 343 can be attached to an obturator hub 103 using welding, bonding, adhesive, or the like. A longitudinal length of the obturator 304 can be the same or longer than the longitudinal length of the needle lumen 251. As such, when the obturator hub 103 engages the needle hub 203, a distal tip of the obturator 304 can extend distally of the lumen opening 260. In an embodiment, the distal tip 346 can be cut or ground down to provide a beveled surface 347 to the obturator 304 that is flush with the beveled face 247, as shown in FIG. 3E.

Advantageously, the obturator 304 also provides a simplified manufacturing process. Initially, there is no requirement for a shield 105 since the flexibility of the obturator 304 prevents needle stick injuries. This simplifies the manufacture process, and provides a smaller access assembly 109. The manufacture of the obturator 304 is further simplified since there is no need for the formation of a recess 150 in the obturator 304 for engaging the shield 105, nor the annular groove 227 (FIG. 1B) that retains the shield within the needle hub 203, or similar detailed structures. These detailed structures cannot be molded into place due to the size and precision required. Instead, these require additional steps to machine such features into place that add to the cost and complexity.

The manufacture of the obturator 304 is also simplified by only requiring a single base length of obturator that can easily be trimmed to suite any length of needle. For example, the flexible obturator 304 can negotiate the rounded region 248 and angled opening 260 of the needle 204, to be advanced distally of a distal tip 246 thereof. The flexible obturator 304 can then be trimmed to size and provide a beveled tip that is flush with the distal face 247 of the needle 204. This removes the need to form different obturators of different sizes to suit different needles and simplifies the manufacturing process. As shown in FIG. 2B, the axis lines 50 illustrate the inner diameter (x) of the needle lumen 251. The rounded region 248 and angled opening 260 can obstruct a rigid obturator from being advanced distally of a distal tip 246 of the needle 204. As such, rigid obturators can be pre-formed with a rounded portion 146 and beveled distal surface 147 to match the rounded portion 246 and beveled surface 247 of the needle lumen, prior to being assembled with the needle 204. As such different lengths of rigid obturators are required to suit different length needles.

Advantageously, the manufacturing process is further simplified in that a flexible obturator 304 can be attached to the obturator hub 103 before assembly with the needle 204 and before being trimmed. When fitting an obturator, e.g. obturator 104, to the needle 204 followed by attaching the obturator hub 103, the obturator can inadvertently adhere to additional structures, e.g. shield 105, needle hub 203, causing the access assembly to fail during use. Optionally, the flexible obturator 304 can also be attached to the obturator hub 103 after assembly with the needle 204. In an embodiment, the obturator tip 304 is trimmed prior to assembly with the needle 204. Advantageously, this prevents the tip of the needle being damaged or blunted during the trimming of the obturator after assembly with the needle.

In an embodiment, the access assembly 109 can further include a lumen clearing mechanism (not shown) that allows the obturator 304 to move slightly, along the longitudinal axis, relative to the needle 204. Advantageously, this allows a user to activate the lumen clearing mechanism after the needle 204 has been placed to advance the obturator 304 relative to the needle 204 and clear any material disposed within the needle lumen 251. As discussed herein, the flexible properties of the obturator 304 allow a distal portion to be advanced through the distal opening 260. In an embodiment, the lumen clearing mechanism is triggered automatically as part of the process of removing the obturator 304 from the needle 204. For example, the lumen clearing mechanism can be activated with the obturator hub 103 is detached from the needle hub 203.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An access assembly for use with an intraosseous access device, comprising:
   a needle including a rounded distal region extending radially inward toward a central axis of the needle to define a beveled distal opening, the needle including a needle lumen;
   an obturator initially disposed in the needle lumen, the obturator formed of a flexible material configured to prevent material from entering the needle lumen by conforming to an inner profile of the needle lumen;
   a needle hub attached to the needle, the needle hub including an external keyed coupling surface extending circumferentially around the needle hub; and
   an obturator hub attached to the obturator, the obturator hub including an internal keyed coupling surface extending circumferentially around a cavity of the obturator hub,
   wherein the internal keyed coupling surface is configured to operatively couple with the external keyed coupling surface to define a fixed angular orientation between the needle hub and the obturator hub.

2. The access assembly according to claim 1, wherein the obturator includes a distal tip that conforms to the beveled distal opening of the needle, wherein the distal tip lies flush with the beveled distal opening.

3. The access assembly according to claim 1, wherein the obturator comprises a distal surface extending perpendicular to a longitudinal axis.

4. The access assembly according to claim 1, wherein the obturator comprises a curved distal surface.

5. The access assembly according to claim 1, further including a beveled distal surface configured to align with the beveled distal opening of the needle.

6. The access assembly according to claim 1, wherein the flexible material displays relatively low columnar strength, low shear strength and high compressive strength.

7. The access assembly according to claim 1, wherein the flexible material includes one of a plastic, a polymer, a thermoplastic, a Polytetrafluoroethylene ("PTFE"), a Polyethylene ("PE"), a Polyurethane ("PU"), a rubber, a silicone, a metal, an alloy, or a Nitinol.

8. The access assembly according to claim 1, wherein the needle hub defines a hub lumen in fluid communication with the needle lumen, and a distal tip of the obturator extends through the needle lumen and further extends distally of the beveled distal opening of the needle when the obturator hub is coupled with the needle hub.

9. The access assembly according to claim 1, further including a lumen clearing mechanism, configured to advance the obturator relative to the needle lumen to clear material from a distal portion of the needle lumen.

10. The access assembly according to claim 9, wherein the lumen clearing mechanism is automatically triggered when the obturator is removed from the needle lumen.

* * * * *